United States Patent

Nedelec et al.

[11] 4,078,059
[45] Mar. 7, 1978

[54] NOVEL 2,2-DIMETHYL STEROIDS

[75] Inventors: Lucien Nedelec, Le Raincy; Vesperto Torelli, Maisons-Alfort; Robert Fournex, Paris, all of France

[73] Assignee: Roussel UCLAF, Paris, France

[21] Appl. No.: 719,138

[22] Filed: Aug. 31, 1976

[30] Foreign Application Priority Data

Sep. 2, 1975 France .............................. 75 26859

[51] Int. Cl.² ..................... C07J 5/00; A61K 31/56
[52] U.S. Cl. .............................. 424/242; 260/397.3; 260/397.47
[58] Field of Search ..................... 260/397.3, 397.47

[56] References Cited

FOREIGN PATENT DOCUMENTS 803,777  10/1958  United Kingdom .............. 260/397.3

Primary Examiner—Elbert L. Roberts
Attorney, Agent, or Firm—Hammond & Littell

[57] ABSTRACT

Novel 2,2-dimethyl steroids of the formula

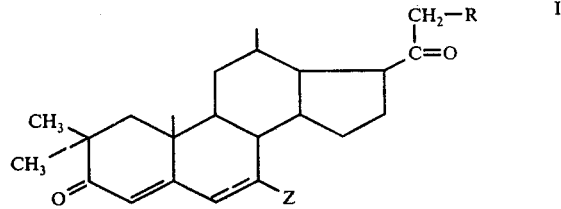

wherein R is selected from the group consisting of hydrogen, —OH and

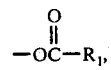

$R_1$ is selected from the group consisting of hydrogen and hydrocarbon of 1 to 17 carbon atoms Z is selected from the group consisting of hydrogen and

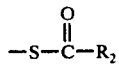

in the α-position, $R_2$ is alkyl of 1 to 4 carbon atoms and the dotted line in the B ring indicates the optional presence of a double bond in the 6(7) position having antialdosterone activity and increasing sodium diuresis while conserving organic potassium.

16 Claims, No Drawings

NOVEL 2,2-DIMETHYL STEROIDS

OBJECTS OF THE INVENTION

It is an object of the invention to provide the novel 2,2-dimethyl steroids of formula I and a novel process for their preparation.

It is a further object of the invention to provide novel therapeutic compositions and to provide a method of treating hypertension and cardiac insufficiency in warm-blooded animals.

These and other objects and advantages of the invention will become obvious from the following detailed description.

THE INVENTION

The novel 2,2-dimethyl steroids of the invention have the formula

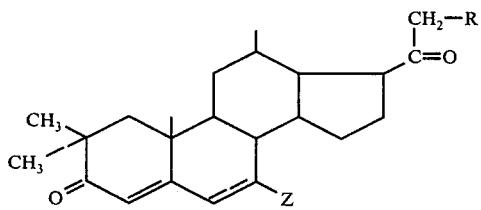

wherein R is selected from the group consisting of hydrogen, —OH and

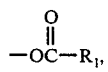

$R_1$ is selected from the group consisting of hydrogen and hydrocarbon of 1 to 17 carbon atoms, Z is selected from the group consisting of hydrogen and

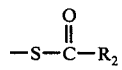

in the α-position, $R_2$ is alkyl of 1 to 4 carbon atoms and the dotted line in the B ring indicates the optional presence of a double bond in the 6(7) position.

When R is

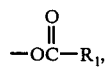

it is preferably an acyloxy of a saturated or unsaturated aliphatic or cycloaliphatic acid and especially alkanoic acid like acetic acid, propionic acid, butyric acid, isobutyric acid and undecylic acid; cycloalkylcarboxylic acid and cycloalkanoic acid like cyclopropylcarboxylic acid, cyclopentylcarboxylic acid, cyclohexylcarboxylic acid, cyclopentylacetic acid, cyclohexylacetic acid, cyclopentylpropionic acid, cyclohexylpropionic acid, benzoic acid; phenylalkanoic acid like phenylacetic acid and phenylpropionic acid. $R_2$ is preferably methyl or ethyl.

Among the preferred compounds of formula I are those where Z is hydrogen, those without ethylenic unsaturation in the B ring and those where the B ring has a doublebond in the 6(7) position.

The novel process of the invention for the preparation of the compounds of formula I wherein Z is hydrogen comprises reacting 20,20-ethylenedioxy-Δ⁴-pregnene-3-one with a methyl halide in the presence of a basic agent at a low temperature to obtain 2,2-dimethyl-20,20-ethylenedioxy-Δ⁴-pregnene-3-one and subjecting the latter to a deketalization agent to form 2,2-dimethyl-Δ⁴-pregnene-3,20-dione which if desired, either may be reacted with lead tetraacetate to form 2,2-dimethyl-21-acetoxy-Δ⁴-pregnene-3,20-dione which may be reacted with a saponification agent to form 2,2-dimethyl-Δ⁴-pregnene-21-ol-3,20-dione which may be reacted with an acid or functional derivative thereof of the formula

where $R_1$ is hydrogen or hydrocarbon of 1 to 17 carbon atoms to obtain the corresponding 2,2-dimethyl-21-acyloxy-Δ⁴-pregnene-3,20-dione; or may be reacted with a deshydrogenation agent to form 2,2-dimethyl-Δ⁴,⁶-pregnadiene-3,20-dione which may also be reacted with lead tetraacetate to obtain 2,2-dimethyl-21-acetoxy-Δ⁴,⁶-pregnadiene-3,20-dione which may be reacted with a saponification agent to form 2,2-dimethyl-Δ⁴,⁶-pregnadiene-21-ol-3,20-dione which may be reacted with an acid of the formula

or a functional derivative thereof to form the corresponding 2,2-dimethyl-21-acyloxy-Δ⁴,⁶-pregnadiene-3,20-dione.

The various 2,2-dimethyl-Δ⁴,⁶-pregnadiene-3,20-dione may be reacted with a thioalkanoic acid of formula

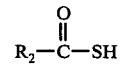

wherein $R_2$ is alkyl of 1 to 4 carbon atoms to form the corresponding compound with a

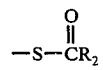

group in the 7α-position.

In a preferred embodiment of the process of the invention, the methyl halide is methyl iodide and the basic agent is an alkali metal alcoholate such as potassium tert.-butylate. The reaction is preferably effected in an aprotic solvent such as tetrahydrofuran. The deketalization agent is preferably an acid such as hydrochloric acid, sulfuric acid, acetic acid, citric acid or p-toluene sulfonic acid and is effected in at least one solvent such as methanol, ethanol, isopropanol or a ketone like acetone.

The reaction with lead tetraacetate is effected in the presence of a boron trifluoride-etherate complex. The saponification agent is preferably an alkali metal base such as sodium hydroxide, potassium hydroxide, potassium carbonate or potassium bicarbonate and the saponification is preferably effected in a lower alkanol such as methanol or ethanol. The functional derivative of the acid is preferably the acid halide such as the acid bromide or chloride but the acid anhydride may also be used.

The deshydrogenation agent is preferably a p-benzoquinone such as chloranil or 2,3-dichloro-5,6-dicyanobenzoquinone. The thioalkanoic acid is preferably one where $R_2$ is methyl, ethyl, n-propyl or n-butyl and the reaction with the $\Delta^{4,6}$-pregnadiene is effected in hot methanol preferably.

The starting compound 20,20-ethylenedioxy-$\Delta^4$-pregnene-3-one is described by Brown et al., Exp., Vol. 18 (1962), p. 309.

The novel therapeutic compositions of the invention are comprised of an effective amount of at least one compound of formula I and an inert pharmaceutical carrier. The compositions may be in the form of tablets, coated tablets, cachets, capsules, granules, emulsions, syrups, suppositories and injectable solution or suspensions.

Examples of the usual pharmaceutical excipients are talc, arabic gum, lactose, starch, magnesium stearate, cacao butter, aqueous and non-aqueous vehicles, fatty bodies of animal or vegetable origin, paraffinic derivatives, glycols, preservatives or diverse wetting agents, dispersants or emulsifiers.

The compositions of the invention are antagonists to aldosterone and increase sodium diuresis while conserving organic potassium. They are useful for the treatment of arterial hypertension and cardiac insufficiencies.

Among the preferred compositions are those where Z is hydrogen and the B ring is saturated or contains a double bond in the 6(7) position. Most preferred is 2,2-dimethyl-$\Delta^4$-pregnene-21-ol-3,20-dione.

The novel method of the invention for the treatment of hypertension and cardiac insufficiency in warm-blooded animals, including humans, comprises administering to warm-blooded animals an effective amount of at least one compound of formula I. The compounds may be administered orally, rectally, or parenterally and the usual useful dose is 0.2 to 20 mg/kg depending the method of administration.

In the following examples there are described several preferred embodiments to illustrate the invention. However, it should be understood that the invention is not intended to be limited to the specific embodiments.

EXAMPLE 1

2,2-dimethyl-$\Delta^4$-pregnene-3,20-dione

STEP A: 2,2-dimethyl-20,20-ethylenedioxy-$\Delta^4$-pregnene-3-one

A solution of 12 g of potassium tert.-butylate in 60 ml of tetrahydrofuran was added under a nitrogen atmosphere with stirring to a solution of 8 g of 20,20-ethylenedioxy-$\Delta^4$-pregnene-3-one [prepared by method of Brown et al, Exp. Vol. 18 (1962), p. 309] in 50 ml of tetrahydrofuran and 25 ml of methyl iodide cooled to $-60°$ C and the mixture was stirred for 45 minutes at $-60°$ C and was then poured into ice water. The mixture was extracted with ethyl acetate to obtain an almost quantitative yield of 2,2-dimethyl-20,20-ethylenedioxy-$\Delta^4$-pregnene-3-one which after crystallized from ethyl acetate melted at $182°-183°$ C.

STEP B: 2,2-dimethyl-$\Delta^4$-pregnene-3,20-dione 3 g of the product of Step A were added to 50 ml of a solution of 135 ml of acetic acid, 20 ml of distilled water and 5 ml of concentrated hydrochloric acid and the mixture was heated to $40°$ C for an hour. The mixture was then concentrated to a small volume and was diluted with water. The oily precipitate formed was extracted with methylene chloride and the extracts were washed with water, dried and evaporated to dryness. The residue was chromatographed over silica gel and was crystallized to obtain 2.13 g of 2,2-dimethyl-$\Delta^4$-pregnene-3,20-dione melting at $160°$ C.

EXAMPLE 2

2,2-dimethyl-21-acetoxy-$\Delta^4$-pregnene-3,20-dione 1.65 ml of boron trifluoride-etherate and then 435 mg of lead tetraacetate impregnated with about 10% of acetic acid were added to a solution of 300 mg of 2,2-dimethyl-$\Delta^4$-pregnene-3,20-dione, 19 ml of benzene and 1 ml of methanol and the mixture was stirred at room temperature for 4 hours. 110 mg of lead tetraacetate were added thereto and the mixture was stirred for another hour and was poured into water. The mixture was extracted with ethyl acetate and the organic extracts were washed with aqueous sodium bicarbonate solution, dried and evaporated to dryness under reduced pressure to obtain 170 mg of 2,2-dimethyl-21-acetoxy-$\Delta^4$-pregnene-3,20-dione which after crystallization from isopropanol melted at $144°$ C.

EXAMPLE 3

2,2-dimethyl-$\Delta^4$-pregnene-21-ol-3,20-dione

A solution of 0.5 g of potassium bicarbonate in 5 ml of water were added under a nitrogen atmosphere to a refluxing mixture of 2 g of 2,2-dimethyl-21-acetoxy-$\Delta^4$-pregnene-3,20-dione in 40 ml of methanol and the mixture was refluxed for one hour and was then diluted with water. The mixture was extracted with methylene chloride and the organic extracts were washed with water, dried and evaporated to dryness to obtain 1.27 g of 2,2-dimethyl-$\Delta^4$-pregnene-21-ol-3,20-dione which after crystallization from a mixture of methylene chloride and isopropyl ether melted at $126°$ C.

EXAMPLE 4

2,2-dimethyl-$\Delta^{4,6}$-pregnadiene-3,20-dione 100 ml of benzene were distilled from 5.7 g of p-toluene sulfonic acid in 200 ml of benzene and then 5.13 of 2,2-dimethyl-$\Delta^4$-pregnene-3,20-dione were added thereto. Then 4.25 g of dichlorodicyanoquinone were added in 3 parts to the refluxing mixture and the mixture was refluxed for 30 minutes and was cooled. The resulting precipitate was filtered and was rinsed with benzene. The filtrate was washed with water, with N/10 sodium hydroxide solution and with water and was then evaporated to dryness. The red oil residue was chromatographed over silica gel to obtain 4.7 g of product which was crystallized from methanol to obtain 2.52 g of 2,2-dimethyl-$\Delta^{4,6}$-pregnadiene-3,20-dione melting at $165°$ C.

EXAMPLE 5

2,2-dimethyl-21-acetoxy-$\Delta^{4,6}$-pregnadiene-3,20-dione 3.2 ml of methanol, 9.9 g of boron trifluorideetherate and 4.83 g of lead tetraacetate were added to a solution of 2.67 g of 2,2-dimethyl-$\Delta^{4,6}$-pregnadiene-3,20-dione in 150 ml of benzene and the mixture was stirred for 24 hours at room temperature. The mixture was poured into an iced aqueous solution of sodium bicarbonate and the organic phase was washed with water, dried and evaporated to dryness. The residue was chromatographed and the product was crystallized to obtain 1.83 g of 2,2-dimethyl-21-acetoxy-$\Delta^{4,6}$-pregnadiene-3,20-dione melting at $156°$ C.

EXAMPLE 6

2,2-dimethyl-$\Delta^{4,6}$-pregnadiene-21-ol-3,20-dione

A solution of 450 mg of potassium bicarbonate in 4.5 ml of water was added to a refluxing mixture of 1.64 g of 2,2-dimethyl-21-acetoxy-$\Delta^{4,6}$-pregnadiene-3,20-dione in 33 ml of methanol and the mixture was refluxed for an hour. 0.5 ml of acetic acid were added thereto and the methanol was distilled. The mixture was diluted with water and extracted with methylene chloride. The organic extracts were evaporated and the residue was chromatographed over silica gel to obtain 1.25 g of 2,2-dimethyl-$\Delta^{4,6}$-pregnadiene-21-ol-3,20-dione melting at 139° C.

EXAMPLE 7

2,2-dimethyl-7α-acetylthio-$\Delta^4$-pregnene-21-ol-3,20-dione

A mixture of 4.2 g of 2,2-dimethyl-$\Delta^{4,6}$-pregnadiene-21-ol-3,20-dione, 32 ml of methanol and 4 ml of thioacetic acid was refluxed for 3 hours and was then evaporated to dryness. The residue was taken up in 10 ml of methylene chloride and 40 ml of isopropyl ether were added thereto. The mixture was concentrated, iced and vacuum filtered. The recovered crystals were crystallized from isopropanol to obtain 2.25 g of 2,2-dimethyl-7α-acetylthio-$\Delta^4$-pregnene-21-ol-3,20-dione melting at 184° C and then 205° C and having a specific rotation of $\alpha_D^{20} = -32° \pm 1.5°$ ($c = 0.8\%$ in $CHCl_3$).

Analysis: $C_{25}H_{36}O_4S$ Calculated: %C 69.41 %H 8.39 %S 7.41 Found: 69.5 8.7 7.4

EXAMPLE 8

2,2-dimethyl-21-propionyloxy-$\Delta^4$-pregnene-3,20-dione 0.74 ml of propionyl chloride was added over 5 minutes at 20° C to a solution of 1.5 g of 2,2-dimethyl-$\Delta^4$-pregnene-21-ol-3,20-dione in 6 ml of pyridine and the mixture was stirred at 20° C for 90 minutes. The mixture was diluted with iced water and was extracted with ethyl acetate. The organic extracts were washed with diluted hydrochloric acid, with water and with aqueous sodium chloride, dried and evaporated to dryness. The residue was chromatographed over silica gel and was eluted with a 9-1 benzene-ethyl acetate mixture to obtain 1.53 g of 2,2-dimethyl-21-propionyloxy-$\Delta^4$-pregnene-3,20-dione which after crystallization from isopropyl ether melted at 114° C and had a specific rotation of $\alpha_D^{20} = +136° \pm 2.5°$ ($c = 1\%$ in $CHCl_3$).

Analysis: $C_{26}H_{38}O_4$ Calculated: %C 75.32 %H 9.24 Found: 75.4 9.1

EXAMPLE 9

Tablets were prepared consisting of 50 mg of 2,2-dimethyl-$\Delta^4$-pregnene-21-ol-3,20-dione and sufficient excipient consisting of talc, starch and magnesium stearate.

PHARMACOLOGICAL DATA

Antialdosterone Activity in rats

Male rats of the Sprague Dawley strain weighing about 180 g were surrenalectomized. Starting from that moment, the rats received physiological serum as drinking water. After 4 days the animals were not fed for 16 hours and received an aqueous solution containing 5% glucose as drinking water.

The 2,2-dimethyl-$\Delta^4$-pregnene-21-ol-3,20-dione was then administered orally at the end of the 16 hours in the form of a 0.25% suspension or solution in carboxymethylcellulose. One hour after this oral administration, the animals received on one hand a hydrosaline surcharge intraperitoneally at a rate of 5 ml per 100 g of body weight, of 0.9% physiological serum and on the other hand 1 μg/kg of a 2.5% alcoholic solution of aldosterone monoacetate subcutaneously. The animals were placed in diuresis cages without food or drinking water for 4 hours. At the end of this time, a forced urination was effected by pressure on the bladder and the volume of urine received was brought up to 50 ml. The amount of sodium and potassium were determined with an autoanalyzer.

The results obtained are expressed as the percent of inhibition of the activity of 1 μg/kg of aldosterone monoacetate administered subcutaneously with respect to the ratio of $$\frac{\text{sodium concentration}}{\text{potassium concentration}}$$

of the surrenalectomized rats and the results are reported in Table I.

TABLE I

| Compound of Example | Oral dose in mg/kg | % inhibition |
|---|---|---|
|  | 2 | 17 |
| 3 | 5 | 39 |
|  | 10 | 100 |

The results of Table I shows that the compound of Example 3 possesses interesting antialdosterone activity when orally administered.

Various modifications of the products and methods of the invention may be made without departing from the spirit or scope thereof and it is to be understood that the invention is intended to be limited only as defined in the appended claims.

We claim:
1. A compound of the formula

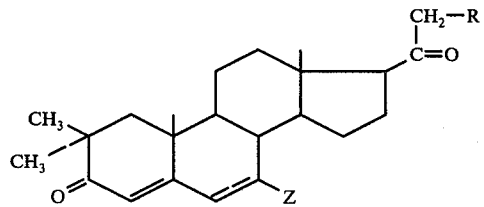

wherein R is selected from the group consisting of hydrogen, —OH and

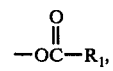

$R_1$ is selected from the group consisting of hydrogen and hydrocarbon of 1 to 17 carbon atoms, Z is selected from the group consisting of hydrogen and

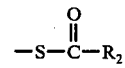

in the α-position, $R_2$ is alkyl of 1 to 4 carbon atoms and the dotted line in the B ring indicates the optional presence of a double bond in the 6(7) position.

2. A compound of claim 1 wherein Z is hydrogen.

3. A compound of claim 2 wherein the B ring is saturated.

4. A compound of claim 2 wherein the B ring has a double bond in the 6(7) position.

5. A compound of claim 1 which is 2,2-dimethyl-$\Delta^4$-pregnene-3,20-dione.

6. A compound of claim 1 which is 2,2-dimethyl-21-acetoxy-$\Delta^4$-pregnene-3,20-dione.

7. A compound of claim 1 which is 2,2-dimethyl-$\Delta^4$-pregnene-21-ol-2,20-dione.

8. A compound of claim 1 which is 2,2-dimethyl-$\Delta^{4,6}$-pregnadiene-3,20-dione.

9. A compound of claim 1 which is 2,2-dimethyl-21-acetoxy-$\Delta^{4,6}$-pregnadiene-3,20-dione.

10. A compound of claim 1 which is 2,2-dimethyl-$\Delta^{4,6}$-pregnadiene-21-ol-3,20-dione.

11. A compound of claim 1 which is 2,2-dimethyl-7$\alpha$-acetylthio-$\Delta^4$-pregnene-21-ol-3,20-dione.

12. A compound of claim 1 which is 2,2-dimethyl-21-propionyloxy-$\Delta^4$-pregnene-3,20-dione.

13. A composition for the treatment of hypertension and cardiac insufficiency comprising an effective amount of at least one compound of claim 1 and an inert pharmaceutical carrier.

14. A composition of claim 13 wherein the compound is 2,2-dimethyl-$\Delta^4$-pregnene-21-ol-3,20-dione.

15. A method of treating hypertension and cardiac insufficiency in warm-blooded animals comprising administering to warm-blooded animals an effective amount of at least one compound of claim 1.

16. The method of claim 15 wherein the compound is 2,2-dimethyl-$\Delta^4$-pregnene-21-ol-3,20-dione.

* * * * *